(12) United States Patent
Yang et al.

(10) Patent No.: US 8,128,953 B2
(45) Date of Patent: Mar. 6, 2012

(54) CONDUCTIVE THERAPEUTIC COATING FOR MEDICAL DEVICE

(75) Inventors: Zhongping Yang, Woodbury, MN (US); Genevieve Louise Eichenberg Gallagher, Mendota Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 139 days.

(21) Appl. No.: 12/183,148

(22) Filed: Jul. 31, 2008

(65) Prior Publication Data

US 2009/0047413 A1  Feb. 19, 2009

Related U.S. Application Data

(60) Provisional application No. 60/956,068, filed on Aug. 15, 2007.

(51) Int. Cl.
*A61N 1/375* (2006.01)
*A61N 1/39* (2006.01)

(52) U.S. Cl. ......... 424/423; 424/489; 427/453; 427/474

(58) Field of Classification Search .................. None
See application file for complete search history.

(56) References Cited

U.S. PATENT DOCUMENTS

| 7,191,009 | B2 | 3/2007 | Laske | |
|---|---|---|---|---|
| 7,320,799 | B2 | 1/2008 | Zhang | |
| 7,887,681 | B2 * | 2/2011 | Zhou | 204/292 |
| 2004/0186528 | A1 | 9/2004 | Ries | |
| 2005/0245971 | A1 * | 11/2005 | Brockway et al. | 607/2 |
| 2007/0089992 | A1 * | 4/2007 | Zhou | 205/109 |
| 2007/0092750 | A1 * | 4/2007 | Zhou | 428/670 |
| 2007/0131318 | A1 * | 6/2007 | Broadley et al. | 148/556 |
| 2007/0207335 | A1 * | 9/2007 | Karandikar et al. | 428/560 |
| 2007/0298377 | A1 * | 12/2007 | Kenealy et al. | 433/173 |
| 2008/0097270 | A1 * | 4/2008 | Utterberg et al. | 602/42 |
| 2010/0116691 | A1 * | 5/2010 | Papadimitrakopoulos et al. | 205/778 |

FOREIGN PATENT DOCUMENTS

| EP | 640661 | 3/1995 |
|---|---|---|
| WO | WO 99/46002 | 9/1999 |
| WO | WO 9946002 A1 * | 9/1999 |

OTHER PUBLICATIONS

Michael Wagner, "Antimicrobial polymers using metallic silver technology for the medical device industry", Medical Polymers (International Conference), Jun. 6-7, 2006.
Grossner-Schreiber, B., et al., "Fibroblast growth on surface-modified dental implants: and in vitro study", J. Biomed. Mater. Res., Mar. 15. 2003; 64A(4):591-9 (abstract enclosed).
P0027043.01PCT/US2009/050790) PCT Notification of Transmittal of the International Search Report and the Written Opinion of the International Searching Authority, 9 pages, Feb. 24, 2010.

* cited by examiner

*Primary Examiner* — Robert A Wax
*Assistant Examiner* — Olga V Tcherkasskaya
(74) *Attorney, Agent, or Firm* — Carol F. Barry (57) ABSTRACT

An implantable medical device includes a housing and a coating disposed on the housing. The coating includes a conductive carrier and a therapeutic agent, e.g. an anti-infective agent such as silver particles. The conductive carrier can be any suitable conductive material, such as iridium oxide, titanium nitride, diamond-like carbon, graphite, polyaniline, platinum, carbon nanotubes, carbon black, platinum black, or poly 3,4,-ethylenedioxythiophene. Coatings containing iridium oxide and metallic silver particles are effective in inhibiting bacterial growth in vitro.

15 Claims, 7 Drawing Sheets

CONDUCTIVE THERAPEUTIC COATING FOR MEDICAL DEVICE

RELATED APPLICATION

This application claims the benefit of provisional U.S. Application Ser. No. 60/956,068, filed Aug. 15, 2007.

FIELD

This disclosure relates, inter alia, to implantable medical devices. More particularly, it relates to systems, devices and methods for preventing or treating an infection in proximity to medical devices implanted in patients.

BACKGROUND

Infection associated with implantation of medical devices is a serious health and economic concern. Today, infections associated with implanted medical devices are not very common due to care and precautions taken during surgical implantation of the devices. However, when infection associated with an implanted medical device (IMD) does occur, explanting the device is often the only appropriate course of action.

For IMDs having a powered component, such as implantable cardiac pacemakers, cardioverter/defibrillators having pacing capabilities, other electrical stimulators including spinal cord, deep brain, nerve, and muscle stimulators, infusion devices, cardiac and other physiologic sensors, cochlear implants, etc., the powered component is typically enclosed in a housing that is implanted subcutaneously at a surgically prepared site, referred to as a "pocket". Associated devices, such as elongated medical electrical leads or drug delivery catheters, extend from the pocket to other subcutaneous sites or deeper into the body to organs or other implantation sites.

Surgical preparation and implantation are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery, directly to the site before the incision is closed, and prescribe oral antibiotics for the patient to ingest during recovery.

Despite these precautions, infections do occur. In addition, once the pocket becomes infected, the infection can migrate along the lead or catheter to the heart, brain, spinal canal or other location in which the lead or catheter is implanted. Such a migrating infection can become intractable and life-threatening, requiring removal of the IMD in the pocket and associated devices, such as leads and catheters. Removal of a chronically implanted lead or catheter can be difficult and dangerous. Accordingly, aggressive systemic drug treatment is prescribed to treat such infections. However, early detection of infection associated with implanted medical devices may allow for earlier intervention, resulting in fewer device explants.

One approach for preventing such infections is to dispose an anti-infective covering, coating, pouch, or the like about the device prior to implantation. The coating includes an anti-infective agent, such as silver particles or an antibiotic, which can elute from the coating to prevent infection in the subcutaneous pocket in which the device is implanted. While effective in many circumstances, some drawbacks still remain.

For example, for devices in which the device housing serves as a return electrode, such as unipolar pacemakers, defibrillators, neurostimulators and the like, placing a coating or covering about the device inhibits or abolishes conductance of the housing and renders the device and therapy ineffective. Some agents that are conductive, such as silver particles, can be coated directly on such devices. However, the ability to control release rate is diminished relative to polymeric systems. In addition, silver particles directly coated onto a device may suffer from reduced antimicrobial activity due to sterilization and tend to flake off the device.

SUMMARY

The present disclosure describes, inter alia, systems, devices and methods that employ a coating containing a conductive carrier and a therapeutic agent, such as metallic silver particles. Such devices can serve to preserve the conductive properties of an underlying device and may result in improved therapeutic efficacy.

In various embodiments, implantable medical devices include a housing and a coating disposed on the housing. The coating includes a conductive carrier and a therapeutic agent, e.g. an anti-infective agent such as silver particles or antibiotics. The conductive carrier can be any suitable conductive material, such as iridium oxide, titanium nitride, ruthenium oxide, diamond-like carbon, graphite, platinum, carbon nanotubes, carbon black, platinum black, polyyrrole, polyaniline, poly 3,4,-ethylenedioxythiophene, or combinations thereof.

In various embodiments, methods for producing implantable medical devices having a conductive therapeutic coating include depositing therapeutic agent on the device; and depositing a conductive carrier on the therapeutic agent.

In various embodiments, methods for producing implantable medical devices having a conductive therapeutic coating include depositing conductive carrier on the device; and depositing a therapeutic agent on the conductive carrier.

By providing devices, systems and methods that include a conductive therapeutic coating, the conductive properties of underlying devices or portions thereof, such as metallic housings, are not compromised. Accordingly, devices where the housing serves as a return electrode or serves other therapeutic or diagnostic functions relying on conductive properties of the housing may continue to function appropriately. In addition and as shown herein, devices coated with a conductive carrier and a therapeutic agent may have improved therapeutic efficacy relative to devices coated with therapeutic agent alone. These and other advantages will be readily understood from the following detailed descriptions when read in conjunction with the accompanying drawings.

The drawings are not necessarily to scale. Like numbers used in the figures refer to like components. However, it will be understood that the use of a number to refer to a component in a given figure is not intended to limit the component in the other figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein "implanted medical device", "implantable medical device", and the like refer to medical devices that are to be at least partially placed within a patient's body. Typically, such devices, or portions thereof, are placed within the patient's body for a period of time for which it would be beneficial to have a therapeutic agent present on an external surface of the device. For example, a medical device implanted in a patient's body for several hours or more constitutes an implantable medical device for the purposes of this disclosure.

As used herein, "active therapy delivering implantable medical device" or the like means an implantable medical device that includes a power source and electronics operably coupled to the power source to control delivery of therapy to a patient. Non-limiting examples of active therapy delivering implantable medical devices include implantable infusion devices and implantable electrical signal generators, such as cardiac defibrillators, pacemakers, neurostimulators, gastric stimulators, and cochlear implants. Active implantable medical devices typically are used in conjunction with associated implantable medical devices, such as catheters or leads.

The present disclosure describes, inter alia, methods, systems, devices employing a conductive coating disposed on a surface of an implanted device, such as a therapy delivering medical device. The conductive coating includes a therapeutic agent, e.g. an anti-infective agent such as metallic silver particles. The coating as a whole is conductive and will allow for conduction between the surface of the device onto which it is coated and tissue in which the device is implanted. Such a coating may be advantageous in situations where the surface of the device serves as a return electrode or serves any other purpose for which conductance is desired or required. However, it will be understood that a coating as described herein may be applied to implantable medical devices that do not have conductive surfaces or whose conductive surfaces do not serve a therapeutic or diagnostic purpose.

Figure 1:
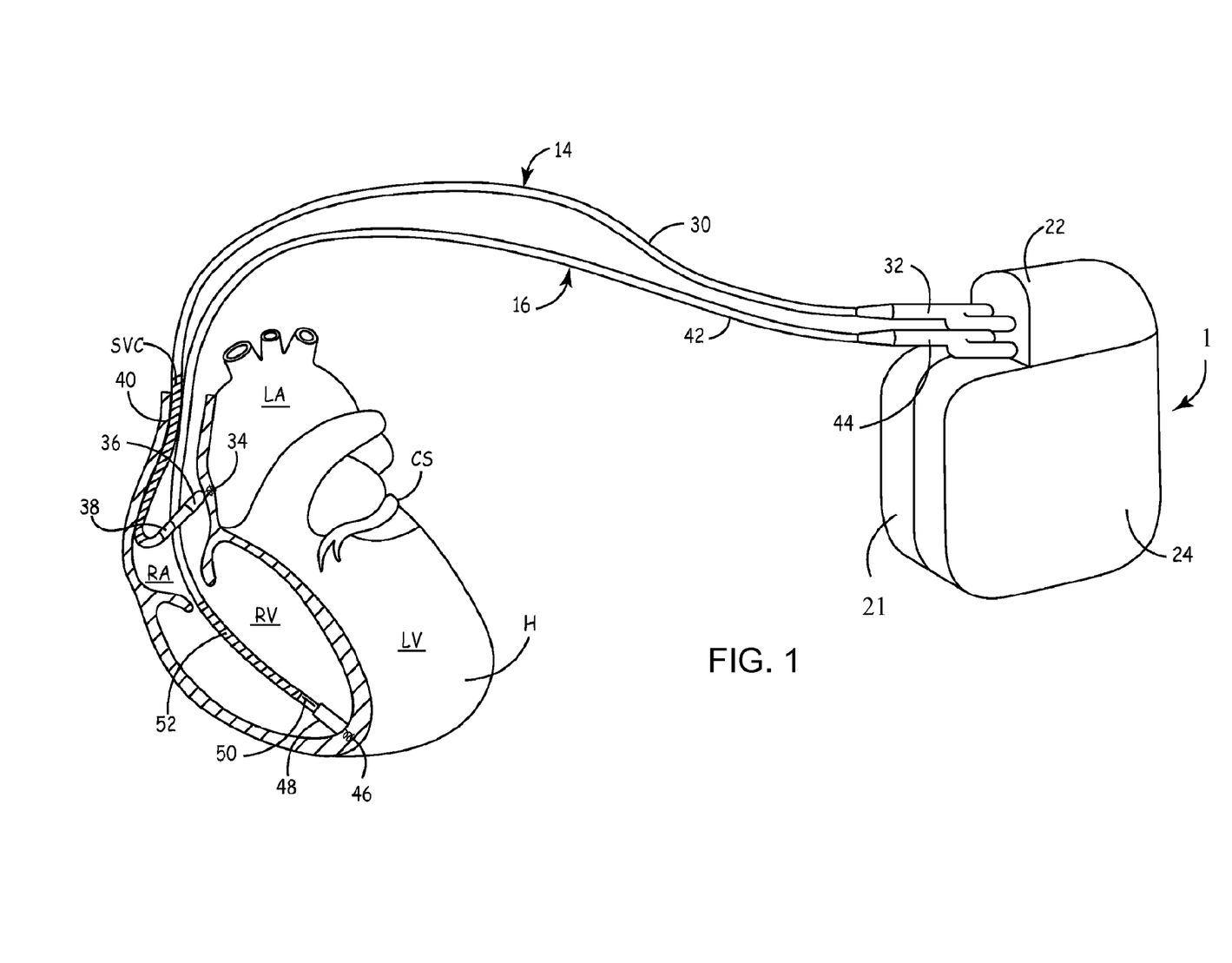
FIG. 1 is a schematic representation of a cardioversion/defibrillation system in conjunction with a heart.
Figure 2:
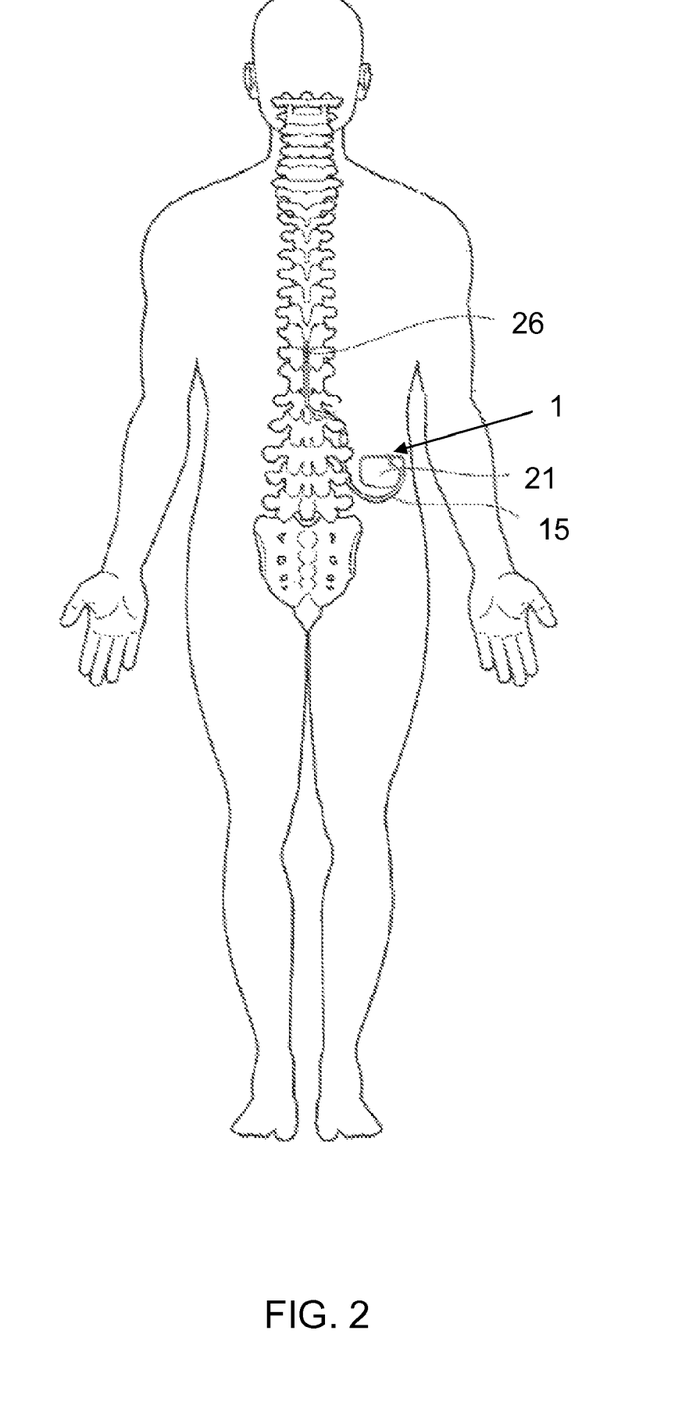
FIG. 2 is a schematic representation of an environment of an electrical signal generator system implanted in a patient

Referring to FIGS. 1 and 2, shown are examples of representative active therapy delivering implantable medical devices 1 and associated devices 20, 20', to which a coating as described herein may be applied. FIG. 1 shows implantable medical device 10, which provides dual chamber pacing and cardioversion/defibrillation therapy to heart H. In FIG. 1, heart H is shown in a partially cutaway view illustrating right atrium RA, left atrium LA, right ventricle RV, left ventricle LV, coronary sinus CS, and superior vena cava SVC. A right atrial (RA) lead 20 and a right ventricular (RV) lead 20' are operably coupled to the depicted implantable cardioverter/defibrillator (ICD) 1. In the embodiment shown in FIG. 1, ICD 1 includes housing or canister 20, header 22, and can electrode 24. The circuitry and power source of ICD 1 are located within housing 20. The circuitry communicates with leads 20 and 20' through electrical connectors within header 22. Can electrode 24 is formed on or is a part of the outer surface of housing 21 and acts as an electrode with respect to one or more of the electrodes carried by leads 20 and 20'.

RA lead 14 is passed through the superior vena cava SVC into right atrium RA of heart H. RA lead 14 includes lead body 30, connector 32, distal tip attachment mechanism 34, tip electrode 36, ring electrode 38, and SVC coil electrode 40. Lead body 30 contains insulated conductors which extend from connector 32 to electrodes 36, 38, and 40. The depicted connector 32 is a bifurcated connector that is inserted into connection bores within header 22 to provide electrical connection between electrodes 36, 38, and 40 and circuitry within ICD 12. Tip electrode 36 and ring electrode 38 are used to deliver pacing pulses to right atrium RA as well as to sense EGM signals within right atrium RA. Coil electrode 40 may be used to deliver a high voltage cardioversion or defibrillation pulse to superior vena cava SVC and right atrium RA. Can electrode 24 is used as the other electrode when a cardioversion/defibrillation pulse is delivered.

RV lead 16 is passed into right atrium RA, and then through the tricuspid valve into right ventricle RV. RV lead 16 includes lead body 42, connector 44, distal tip attachment mechanism 46, tip electrode 48, ring electrode 50, and coil electrode 52. In some embodiments, an SVC coil can be located on RV lead 16 rather than RA lead 14. Lead body 42 of RV lead 16 contains electrically insulated conductors which extend from connector 44 to tip electrode 48, ring electrode 50 and coil electrode 52. At the proximal end of RV lead 16, bifurcated connector 44 is inserted into a pair of connection bores of header 22 to provide electrical connection between the circuitry within housing 21 and electrodes 48, 50, and 52. Tip electrode 48 is placed in contact with the apex of right ventricle RV, and is fixed in place by attachment mechanism 46, which may be, for example, a screw or tined fastener.

Tip electrode 48 and ring electrode 50 form a bipolar electrode pair which can be used for applying pacing pulses to right ventricle RV and sensing EGM signals representing electrical activity in right ventricle RV. Coil electrode 52 is used, in conjunction with can electrode 24 to apply high voltage cardioversion or defibrillation shock in order to halt ventricular arrhythmia. Together with tip electrode 48, coil electrode 52 also forms an integrated bipolar sensing electrode pair which can be used to sense EGM signals.

FIG. 2 depicts an environment of an implantable signal generator device 1, such as Medtronic Inc.'s Restore™ Advanced implantable neurostimulator, and associated lead 15 for use in neuromodulatory therapies. The implantable signal electrical generator 1 is subcutaneously implanted in an abdominal region of a patient. A distal portion of the depicted lead 15 is epidurally placed along a suitable location of spinal cord. Proximal end of the depicted lead 15 is tunneled subcutaneously to location of active device 1, where it may be connected to active device 1. Lead 15 includes one or more electrical contacts (not shown) on its proximal end portion and one or more electrodes on its distal end portion 26. The contacts and electrodes are electrically coupled via conductive wires running through lead 15. Electrical signals generated by the signal generator 1 may be delivered to lead 15 through the contacts and then to the patient through the electrodes. In various embodiments, the electrodes of the lead are configured to apply an electrical signal to the patient in bipolar mode with an electrode or an electrode pair serving as the return electrode. In some embodiments the system is configured to operate in unipolar mode where the housing 21 of the signal generator 1 serves as the return electrode.

In order for the housings 21 of the active implantable devices 1 depicted in the representative systems depicted in FIGS. 1 and 2 to serve as a return electrode, the housing includes at least a portion formed of conductive material. Typically the housings of such active implantable medical devices 1 are formed from titanium and are hermetically sealed to protect the internal electronic components. Of course, the housing may be formed of any suitable material. Other uses for a conductive housing may include use of the housing for sensing electrical or other signals associated with physiological parameters, e.g. for use in determining cardiac activity.

While FIGS. 1 and 2 depict implantable cardioverter/defibrillator and neuromodualtory electrical signal generator systems, it will be understood that the teachings described herein may be applicable to virtually any known or future developed active implantable therapy delivering medical device. It will be further understood that coatings as described herein may be advantageously applied to conductive surfaces of devices, such as metallic surfaces, the coatings may be applied to non-conductive surfaces of devices as well.

Figure 3:
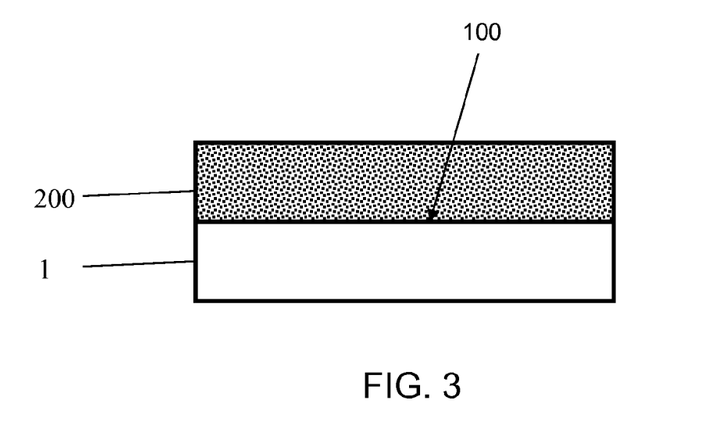
FIGS. 3-5 are a schematic representations of a cross sections of a coated device or portions thereof.

Referring now to FIG. 3, a schematic view of an implantable medical device 1 having a surface 100 coated with a coating 200 is shown. The surface 100 of the device coated may correspond to a housing 21 of the device 1 (e.g. as shown in FIGS. 1 and 2). While shown as being present on only one surface 100 of device 1, coating 200 may be applied to the entire outer surface of device 1 or a portion thereof.

The coating 200 includes a conductive material and a therapeutic agent. The conductive material may be present in the coating material in any suitable amount; e.g., between about 0.1% by weight and about 99.9% by weight. In numerous embodiments, a sufficient amount of conductive material is present in coating 200 to allow for conductance between the surface 100 of the device 1 and tissue in which the device 1 is implanted, if the surface 100 of the device 1 were conductive. Any suitable conductive material may be used as conductive carrier. In various embodiments, the conductive carrier material has a conductance of 0.001 Seimens/cm or greater (in-vivo). Representative examples of suitable conductive materials for use as a conductive carrier include iridium oxide, titanium nitride, diamond-like carbon, graphite, platinum, carbon nanotubes, carbon black, platinum black, ruthenium oxide, polypyrrole, polyaniline, poly 3,4,-ethylenedioxythiophene, and combinations thereof.

The coating may be disposed on the surface 100 of the device 1 in any suitable manner. For example, and referring to FIG. 4, the coating 200 may include a first layer 210 in contact with the surface 100 of the device 1 and a second layer 220 in contact with the first layer 210. In various embodiments, the first layer includes, consists essentially of or consists of therapeutic agent. In numerous embodiments, the first layer includes, consists essentially of or consists of conductive carrier. In various embodiments, the second layer includes, consists essentially of or consists of therapeutic agent. In numerous embodiments, the second layer includes, consists essentially of or consists of conductive carrier.

Figure 4:
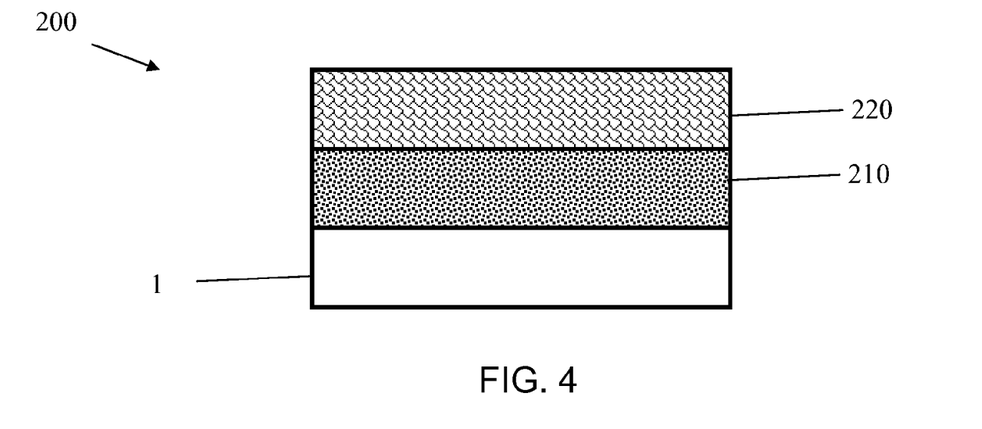

Any suitable process may be employed to obtain a layered coating layer 200. For example, physical or chemical vapor deposition may be employed to deposit conductive carrier or therapeutic agent on the surface of device 1 or on the surface or an underlying coating layer. When vapor deposition is employed, coating layers are typically in the range of between about 10 nanometers and 1 millimeter thick.

Any therapeutic agent may be included in coating 200. Because it may be desirable to treat or prevent infections and/or inflammation associated with implantation of a medical device, it may be desirable to include one or more anti-infective agent or one or more anti-inflammatory agent in coating 200. In addition, in some circumstances it may be desirable to deliver a local anesthetic or an anti-proliferative agent from the surface of an implanted device 1.

Any anti-infective agent may be used in a coating having conductive carrier. The anti-infective agent may be present in coating 200 in any amount such that infection is treated or prevented when device 1 containing the coating 200 is implanted in a patient. Generally, the coating contains between about 0.1% and about 90% by weight of the anti-infective agent. Suitable anti-infective include antibiotics and antiseptics. Any antibiotic suitable for human use may be used in accordance with various embodiments. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin and combinations thereof. Other examples of antibiotics, such as those listed in Sakamoto et al., U.S. Pat. No. 4,642,104, which is herein incorporated by reference in its entirety, may also be used. One of ordinary skill in the art will recognize other antibiotics that may be used.

In general, it is desirable that the selected antibiotic(s) kill or inhibit the growth of one or more bacteria that are associated with infection following surgical implantation of a medical device. Such bacteria are recognized by those of ordinary skill in the art and include *Staphylococcus aureus, Staphylococcus epidermis*, and *Escherichia coli*. Preferably, the antibiotic(s) selected are effective against strains of bacteria that are resistant to one or more antibiotic.

To enhance the likelihood that bacteria will be killed or inhibited, it may be desirable to combine two or more antibiotics. It may also be desirable to combine one or more antibiotic with one or more antiseptic. It will be recognized by one of ordinary skill in the art that antimicrobial agents having different mechanisms of action and/or different spectrums of action may be most effective in achieving such an effect. In an embodiment, a combination of rifampin and micocycline is used. In an embodiment, a combination of rifampin and clindamycin is used.

Any antiseptic suitable for use in a human may be used in accordance with various embodiments. Antiseptic includes disinfectants. Nonlimiting examples of antiseptics include hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde), silver-containing compounds (silver sulfadiazene, silver metal, silver ion, silver nitrate, silver acetate, silver protein, silver lactate, silver picrate, silver sulfate), and alcohols. One of ordinary skill in the art will recognize other antiseptics that may be employed in accordance with this disclosure.

According to various embodiments, antiseptic metallic particles are included in coating 200. Metallic particles, like the conductive carrier, are conductive and may be advantageously used when the surface of the device 1 onto which coating 200 is coated is desired to be conductive. Metallic particles, such as nanoparticles, of silver, silver alloys, copper, copper alloys, zinc, zinc alloys, gallium, gallium alloys, or the like, and combinations thereof may have anti-infective properties. Such particles can generate silver, copper, zinc, gallium, etc. ions when exposed to oxygen and water, such as when implanted in a patient.

Metallic nanoparticles typically range in size from about 1 nm to about 250 nm; e.g., from about 15 nm to about 100 nm, or from about 20 nm to about 80 nm. When metallic particles are included in a coating 200 in which conductive carrier and metallic particles are in a single layer, metallic particles may be present in any amount effective to prevent or treat infection when device 1 is implanted in a patient. For example, metallic particles may be present in an amount between about 0.1 weight percent and about 99.9 weight percent. When metallic particles are included in a coating 200 in which conductive carrier and metallic particles are in separate layers, metallic particles may be present in a layer in any amount effective to prevent or treat infection when device 1 is implanted in a patient. For example, the layer may consist essentially of the metallic particle.

It will be understood that the ratio of conductive carrier to metallic particle may vary depending on the carrier and particle used. For example, it may be desirable to keep concentrations of gallium nitrate low, as it is effective against bacteria at very low concentrations and may cause undesirable changes in pH and osmolarity at higher concentrations. By way of further example, silver nanoparticles may be employed at relatively high concentrations with only a very thin protective layer of conductive carrier.

While not intending to be bound by theory, it is believed that the use of a conductive carrier with metallic particles helps protect the metallic particles from premature oxidation during processing of the device 1, such as sterilization with ethylene oxide. This is believed to be particularly important when the coating 200 consists of two layers 210, 220 and the first layer 210 that contacts the device 1 surface 100 contains the metallic particles and the second outer layer 220 contains the conductive carrier. The outer layer 220 can serve to protect the metallic particles in the inner layer 210 from oxidation.

Again, without intending to be bound by theory, it is believed that when the metallic particles are included in an outer layer 220 of a two layer coating 200, the underlying layer 210 containing conductive carrier may generate a rough surface, increasing the surface area to which the outer layer 220 including the metallic particles may be disposed. Accordingly, it is believed that an increased amount of metallic particles may be loaded. While some of the metallic particles may be sacrificed or oxidized during processing, a sufficient anti-infective amount may remain in the outer layer 220. As shown in the examples below, nanoscale morphology of both a conductive coating layer and a conductive coating layer with an overlaying metallic particle layer is achievable with vapor deposition.

Regardless of the antiseptic employed, it is desirable that the antiseptic(s) selected kill or inhibit the growth of one or more microbes that are associated with infection following surgical implantation of a medical device. Such microbes are recognized by those of ordinary skill in the art and include *Stapholcoccus aureus, Staphlococcus epidermis, Escherichia coli, Pseudomonas aeruginosa*, and *Candidia*.

To enhance the likelihood that microbes will be killed or inhibited, it may be desirable to combine two or more antiseptics. It may also be desirable to combine one or more antiseptics with one or more antibiotics. It will be recognized by one of ordinary skill in the art that antimicrobial agents having different mechanisms of action and/or different spectrums of action may be most effective in achieving such an effect. For example, a combination of chlorohexidine and silver sulfadiazine may be employed.

In various embodiments, an anti-inflammatory agent may be included in a coating 200 along with a conductive carrier. Generally, any anti-inflammatory agent suitable for use in a human may be used. Non-limiting examples of anti-inflammatory agents include steroids, such as prednisone, dexamethasone, and methyl-prednisilone; and non-steroidal anti-inflammatory agents (NSAIDs).

In various embodiments, a local anesthetic agent may be included in a coating 200 along with a conductive carrier. Generally, any local anesthetic agent suitable for use in a human may be used in accordance with various embodiments of the invention. Non-limiting examples of local anesthetics agents include lidocaine, prilocaine, mepivicaine, bupivicaine and articaine.

In various embodiments, an anti-proliferative agent may be included in a coating 200 along with a conductive carrier. Generally, any anti-proliferative agent suitable for use in a human may be used in accordance with various embodiments of the invention. As used herein, "anti-proliferative agents" includes anti-migration agents. In various embodiments, an anti-proliferative agent is an agent capable of preventing restenosis. Examples of anti-proliferative agents include QP-2 (taxol), actinomycin, methotrexate, angiopeptin, vincristine, mitocycin, statins, C-MYC antisense, sirolimus, restenASE, 2-chloro-deoxyadenosine, PCNA (proliferating cell nuclear antigent) ribozyme, batimastat, prolyl hydroxylase inhibitors, halofuginone, C-proteinase inhibitors, probucol, and combinations and/or derivates thereof. In various embodiments, one or more anti-proliferative agent with one or more anti-inflammatory agent.

Of course, one or more therapeutic agent of a given class, such as anti-infective, anti-proliferative or anesthetic, may be combined with one or more therapeutic agents of another class in accordance with the teachings presented herein.

Figure 5:
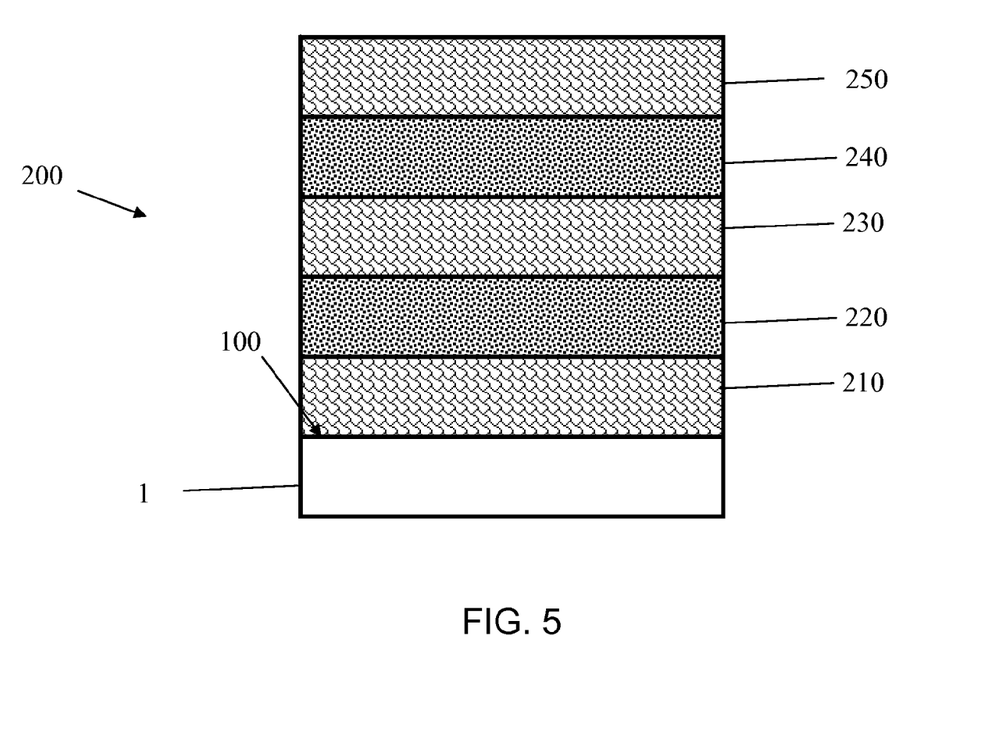

Referring now to FIG. 5, a coating 200 disposed on a surface 100 of an implantable medical device 1 may include three or more layers 210, 220, 230, 240, 250. For example, coating 200 may include alternating layers of conductive carrier and therapeutic agent deposited by vapor deposition. For example, layers 210, 230 and 250 may include, consist essentially of or consist of conductive carrier and layers 220 and 240 may include, consist essentially of or consist of therapeutic agent. Deposition of a layer of material of the same composition as the layer on which is it deposited will be considered, for the purposes of this disclosure, deposition of a single layer.

It will be understood that the patterning of the layers depicted in FIGS. 3-5 is arbitrary and does not necessarily indicate that layers patterned in the same manner in a figure or between figures are composed of the same materials. For example, coating 200 of FIG. 3 does not necessarily contain the same material as layer 210 of FIG. 4, even though the patterning of the layers is the same. By way of further example, layers 220 and 240 of FIG. 5 do not necessarily contain the same material, even though the patterning of the layers is the same.

It will be understood that a surface of a device, such as surface 100 of device 1 as depicted in FIGS. 3-5, may be coated with an intervening coating between device 1 and coating 200. For the purposes of the present disclosure in such cases, the "surface" of the device 1 onto which the coating 200 is applied is the surface of the intervening coating.

In the following, non-limiting examples are presented, which describe various embodiments of the articles and methods discussed above.

EXAMPLES

Example 1

Coating of Titanium Disk Substrates

Titanium disk substrates were punched out of shields of implantable pulse generators (Medtronic, Inc.) and implantable cardioverter/defibrillators (Medtronic, Inc.). The substrates were cleaned in acetone, rinsed in isopropyl alcohol and blown dry prior to coating. Coatings were applied using a physical vapor deposition process. A Perkin Elmer Sputter System was used with a chamber pressure between ~$1 \times 10^{-7}$ and ~$1 \times 10^{-5}$ Torr and the sample table stationary and in the down position. All substrates received a coat of titanium using a titanium sputtering target to promote adhesion of subsequent layers. The following settings were used on the sputtering system to apply the titanium layer: a forward power set point of ≈200 W, a target voltage of ≈260 V, an argon pressure of ≈11.5 mTorr, an argon flow of ≈20 cm$^3$/min, a ramp time of ≈2 minutes, and a deposition time of ≈2.5-3.25 minutes). Samples were coated with silver alone using a silver sputtering target, iridium oxide alone using an iridium oxide target, first with iridium oxide and then with silver, or first with silver and then with iridium oxide. The following settings were used on the sputtering system to apply the iridium oxide layer: a forward power set point of ≈100 W, a target voltage of ≈400 V, an argon pressure of ≈15.5 mTorr, an argon flow of ≈12.5 cm$^3$/min, a ramp time of ≈2 minutes, and a deposition time of ≈1.5-5 minutes. A reactive sputtering mode with a mix of argon and oxygen was used to deposit the iridium oxide. The following settings were used on the sputtering system to apply the silver layer: a forward power set point of ≈100 W, a target voltage of ≈320 V, an argon pressure of ≈11.5 mTorr, an argon flow of ≈20 cm$^3$/min, a ramp time of ≈2 minutes, and a deposition time of ≈0.25-2 minutes. The target thicknesses of each layer were ≈500 Å of titanium, ≈140-280 Å of silver, and ≈1000 Å of iridium oxide. Total coating thicknesses were ≈500-4000 Å.

Figure 6:
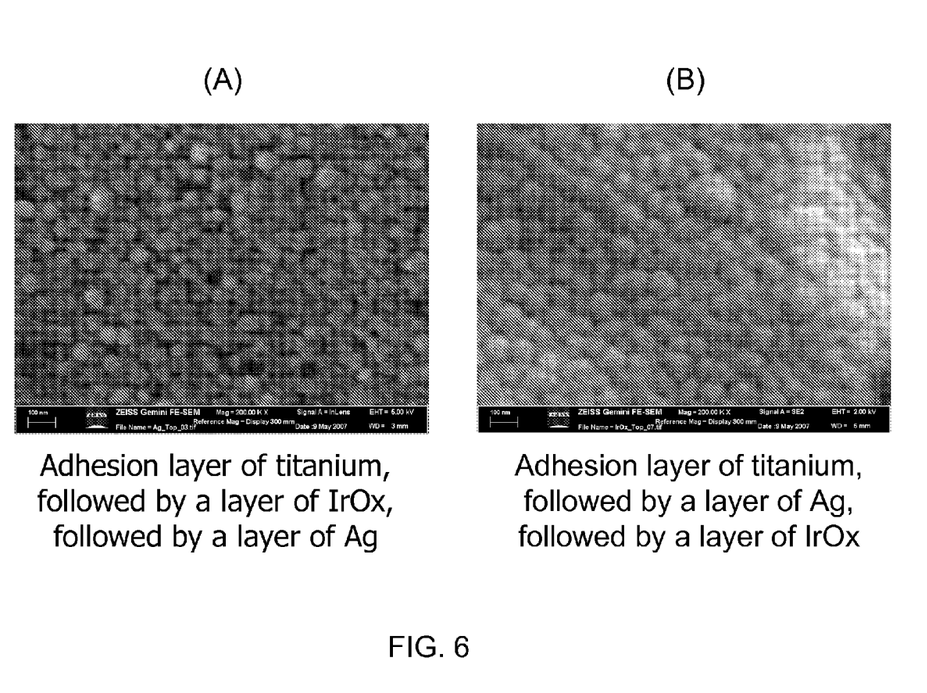
FIGS. 6A-B are images of a scanning electron micrographs of surfaces of titanium disks coated with iridium oxide (A) and iridium oxide and silver nanoparticles (B).

Scanning electron micrograph images were taken of the coated substrates using a Zeiss Gemini FE-SEM, 5.0 kV, 200,000× magnification. As shown in the representative images in FIG. 6, the coated surfaces exhibited nanoscale morphology, which should provide for maximal surface area for the release of silver ions. In addition, the surface appears to be porous, which may allow body fluids to penetrate and allow for controlled release of the underlying silver.

Example 2

Antimicrobial Efficacy

The antimicrobial efficacy of disks created in accordance with Example 1 was tested in vitro using ASTM method E2180-01. Briefly, an 18 hr bacterial culture of *S. aureus* (ATCC 29213) was grown at 37° C. in tryptic soy broth. An agar slurry was prepared by dissolving 0.85 g NaCl and 0.3 g agar-agar in 100 ml of deionized water. The solution was heated on a hot plate until the agar dissolved. The solution was autoclave sterilized. The bacterial suspension was adjusted to $1\text{-}5 \times 10^8$ cells/mL using a 1.0 McFarland turbidity standard (equivalent to ~$3 \times 10^8$ cells/mL). A sterile cotton swab was dipped into sterile 0.85% saline to pre-wet the surfaces and to facilitate the spreading of the inoculum. 1.0 mL of adjusted bacterial suspension was transferred to the agar slurry and equilibrated to 44° C. 0.1 mL of the inoculum was pipetted onto each test/control surface. The agar was allowed to gel and was then placed at 37° C. in a humidified chamber for 6 hours. After exposure, each surface was transferred to individual tubes containing 10 mL of neutralizing broth. The tubes were sonicated for 5 minutes followed by a 1 minute vortex. Ten-fold serial dilutions were performed through $10^{-2}$ dilution for test samples and $10^{-4}$ for control samples. 0.1 mL aliquots were placted, in duplicate, of the $10^0$, $10^{-1}$ and $10^{-2}$ dilutions for all test samples and $10^{-2}$, $10^{-3}$ and $10^{-4}$ dilutions for all control samples. Colony forming units (CFUs) per carrier were calculated as follows: CFUs/carrier=[(avg. cell count)×(dilution factor)×(volume of diluent)×(volume inoculated)]/(volume plated).

Figure 7:
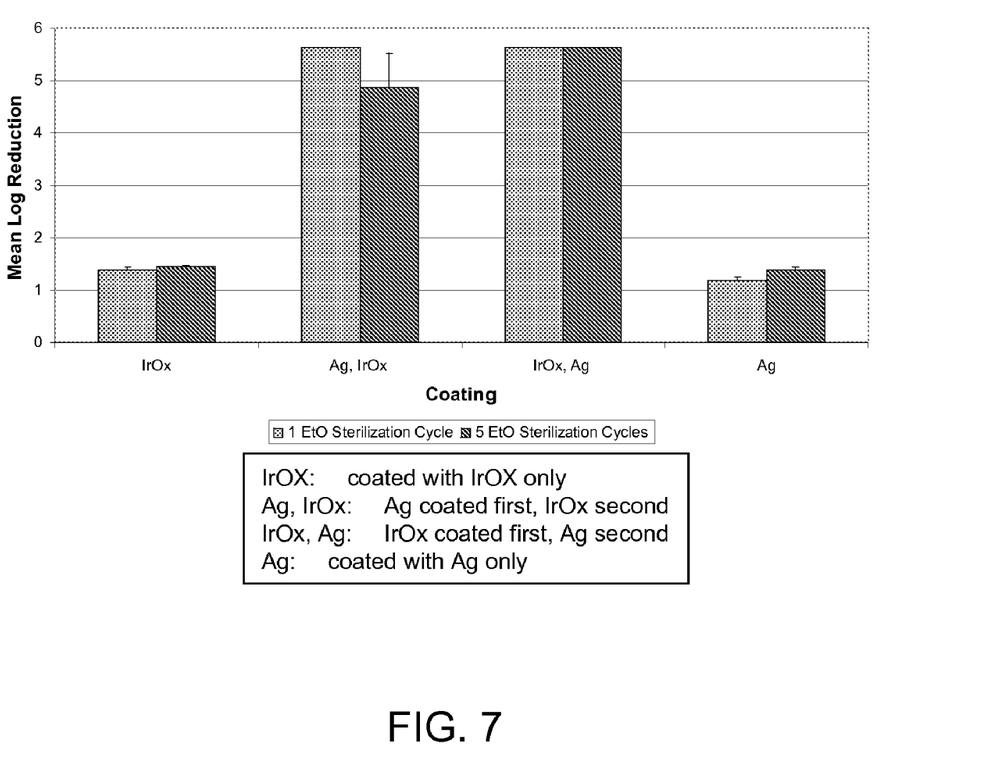
FIGS. 7-8 are graphs showing the ability of coated titanium disks to prevent the growth of S. aureus in-vitro.

As indicated in FIG. 7, disks coated with both iridium oxide and silver, regardless of whether the iridium oxide was deposited first or whether the silver was deposited first, resulted in about a five-fold higher log reduction in *S. aureus* than silver alone.

While not intending to be bound by theory, it is believed that ethylene oxide sterilization resulted in inactivation of the silver on the disks coated with silver without iridium oxide. That is, oxidation of silver during ethylene oxide sterilization may have rendered the silver incapable of generating antimicrobial silver ions. This may explain why the silver coated disks were no more effective than iridium oxide coated disks. This explanation appears to initially be at odds with the results obtained with the disks where silver was deposited on top of the iridium oxide. That is, if exposed silver deposited directly on the surface of a disk is inactivated during sterilization, then exposed silver deposited on iridium oxide deposited on a disk should also be inactivated. One possible explanation for this seemingly contradictory result is that the iridium oxide coating layer produces a nanoscale morphology (see, e.g. FIG. 6), allowing more silver to be coated and released. Perhaps some of the silver was inactivated, but a sufficient amount of readily releasable silver remained to prevent growth of *S. aureus*.

Figure 8:
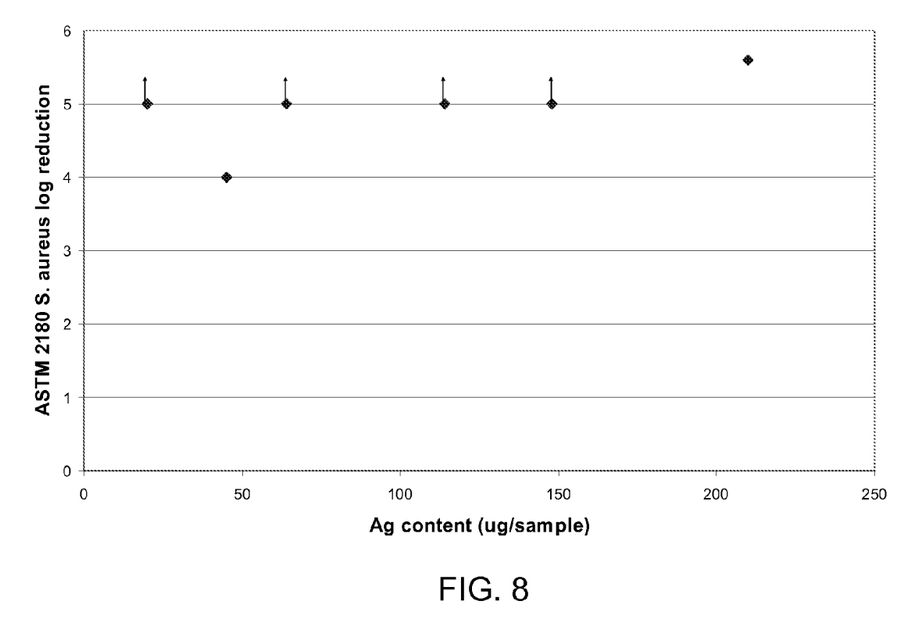

However, it should be noted that amount of silver alone does not appear to be a determining factor in how effectively a coated disk can inhibit growth of bacteria. As shown in FIG. 8, coated disks with varying silver particle content all performed about equally well in the in vitro tests. The samples in the study for FIG. 8 contained an adhesion layer of titanium, followed by a layer of silver, followed by a layer of iridium oxide. As shown in FIG. 8, log reduction of *S. aureus* was roughly equal across an approximately ten fold range in amount of coated silver particles coated.

Figure 9:
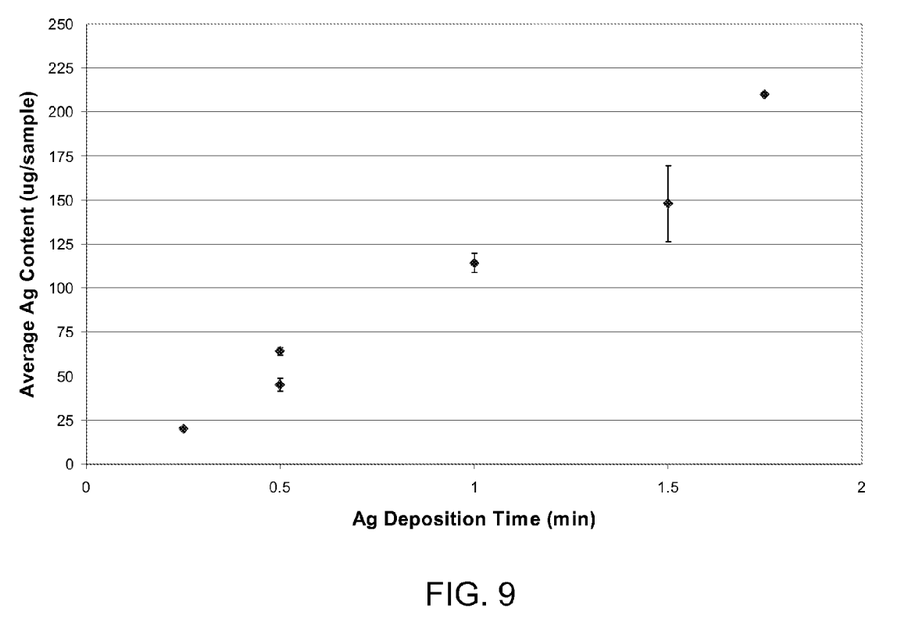
FIG. 9 is a graph showing the relationship between silver deposition time and silver content of the coating.

As shown in FIG. 9, the amount of metal particle deposited may be varied by varying the time that the metal particle is deposited. The samples in the study for FIG. 9 contained an adhesion layer of titanium, followed by a layer of silver, followed by a layer of iridium oxide. The amount of silver particles deposited increased in a roughly linear manner as the time of the deposition was increased.

Referring back to FIG. 7, additional rounds of ethylene oxide sterilization (beyond one round) had little to no effect on the antimicrobial efficacy of the silver coated disks. As such, it appears that any negative effect of ethylene oxide sterilization of the efficacy of the silver is realized in the initial round of sterilization and that further rounds of sterilization do not compound the negative effects.

An in-vivo study of antimicrobial efficacy of a single chamber Medtronic EnPulse™ pacemaker coated with silver and then iridium oxide (generally as described in Example 1, except that devices were cleaned with aqueous detergent solution, isopropyl alcohol and blown dry prior to coating) and a cut silicone lead was also performed. Specifically, a titanium deposition time of 3.25 minutes, a silver deposition time of 0.5 minutes, and an iridium oxide deposition time of 1.5 minutes was used, in that order, to coat the pacemaker. Total coating thickness ranged from ≈500-2500 Å. Devices were implanted subcutaneously into rabbits, and *S. aureus* was injected into the device pocket at the time of implantation. After 28 days the pacemakers, leads, subcutaneous pocket and blood were tested for presence of the bacteria. A twenty five percent reduction in number of occurrences of the presence of the bacteria was observed with the coated pacemakers (6 out of 8 with infection) relative to uncoated (8 out of 8 with infection), which was comparable to pacemaker coated with silver only applied by an external company (5 out of 8 with infection).

Thus, embodiments of the CONDUCTIVE THERAPEUTIC COATING FOR MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device comprising:
a metallic housing;
a coating disposed on the housing; the coating consist of a conductive carrier and a metallic anti-infective agent, wherein the conductive carrier is iridium oxide and the metallic anti-infective agent is silver nanoparticles.

2. The device of claim 1, wherein the coating comprises a first layer in contact with the housing and a second layer in contact with the first layer, wherein the metallic anti-infective agent is disposed in the first layer and the conductive carrier is disposed in the second layer.

3. The device of claim 1, wherein the coating comprises a first layer in contact with the housing and a second layer in contact with the first layer, wherein the metallic anti-infective agent is disposed in the second layer and the conductive carrier is disposed in the first layer.

4. The device of claim 1, wherein the housing serves as a return electrode.

5. The device of claim 1, wherein the device is an active implantable medical device.

6. A system comprising:
the device of claim 5; and
an associated medical lead operably coupleable to the device.

7. A method for producing an implantable medical device having a conductive therapeutic coating; the method comprising:
depositing silver nanoparticles on the metallic device housing of the device; and
depositing iridium oxide on the silver nanoparticles.

8. The method of claim 7, wherein depositing the silver nanoparticles on the device comprises depositing the therapeutic agent by plasma vapor deposition or chemical vapor deposition.

9. A method for producing an implantable medical device having a conductive therapeutic coating; the method comprising:
depositing iridium oxide on the metallic housing of the device; and
depositing a silver nanoparticles on the iridium oxide.

10. An implantable medical device comprising:
a metallic housing;
a coating disposed on the housing; the coating consist of a conductive carrier and an a therapeutic agent, wherein the conductive carrier is iridium oxide and the therapeutic agent is silver nanoparticles,
wherein the coating has a conductance sufficient to allow conduction between the housing and tissue of a patient when the device is implanted in a patient.

11. The implantable medical device of claim 1, wherein the device is an electrical signal generator.

12. The implantable medical device of claim 1, wherein the device is selected from the group consisting of a defibrillator, a pacemaker, and a neurostimulator.

13. The implantable medical device of claim 10, wherein the device is an active implantable medical device.

14. The implantable medical device of claim 10, wherein the device is an electrical signal generator.

15. The implantable medical device of claim 10, wherein the device is selected from the group consisting of a defibrillator, a pacemaker, and a neurostimulator.

* * * * *